US009663539B2

(12) United States Patent
Vu et al.

(10) Patent No.: US 9,663,539 B2
(45) Date of Patent: May 30, 2017

(54) PROCESS FOR PRODUCING LOW-COLOR AND COLOR-STABLE ISOCYANATOORGANOSILANES AND PRODUCTS DERIVED THEREFROM

(71) Applicant: Momentive Performance Materials Inc., Waterford, NY (US)

(72) Inventors: Dung-Thi Vu, Grand Rapids, MI (US); Frank Dominic Mendicino, Marietta, OH (US); Steven Roger Bahr, Williamstown, WV (US); Lina Zhao, Parkersburg, WV (US); Jeffrey R. Kelby, Belpre, OH (US); Vikram Kumar, Tarrytown, NY (US); David Mark Wilcox, Sistersville, WV (US)

(73) Assignee: Momentive Performance Materials Inc., Waterford, NY (US)

( * ) Notice: Subject to any disclaimer, the term of this patent is extended or adjusted under 35 U.S.C. 154(b) by 0 days.

(21) Appl. No.: 14/797,828

(22) Filed: Jul. 13, 2015

(65) Prior Publication Data
US 2016/0009738 A1 Jan. 14, 2016

Related U.S. Application Data

(60) Provisional application No. 62/024,030, filed on Jul. 14, 2014.

(51) Int. Cl.
| | | |
|---|---|---|
| C07F 7/02 | (2006.01) | |
| C07F 7/18 | (2006.01) | |
| C08G 18/60 | (2006.01) | |
| C08G 18/08 | (2006.01) | |

(52) U.S. Cl.
CPC .............. *C07F 7/02* (2013.01); *C07F 7/1836* (2013.01); *C07F 7/1892* (2013.01); *C08G 18/0823* (2013.01); *C08G 18/603* (2013.01)

(58) Field of Classification Search
None
See application file for complete search history.

(56) References Cited

U.S. PATENT DOCUMENTS

| | | | | |
|---|---|---|---|---|
| 3,494,951 A * | 2/1970 | Berger | ................. | C07F 7/0892 106/13 |
| 3,598,852 A | 8/1971 | Berger | | |
| 3,607,901 A * | 9/1971 | Berger | ................. | C07F 7/0892 556/414 |
| 4,654,428 A | 3/1987 | Kurashima et al. | | |
| 4,697,009 A * | 9/1987 | Deschler | ................. | C07F 7/182 540/487 |
| 5,212,133 A | 5/1993 | Duranel et al. | | |
| 5,218,133 A | 6/1993 | Pepe et al. | | |
| 5,393,910 A | 2/1995 | Mui et al. | | |
| 5,731,458 A | 3/1998 | Dahmer et al. | | |
| 5,977,256 A | 11/1999 | Huybrechts et al. | | |
| 6,008,396 A | 12/1999 | Sheridan et al. | | |
| 6,080,816 A | 6/2000 | Gregorovich et al. | | |
| 6,388,117 B2 | 5/2002 | Pinske | | |
| 6,673,954 B1 | 1/2004 | Gedon et al. | | |
| 6,790,904 B2 | 9/2004 | White et al. | | |
| 6,812,316 B2 | 11/2004 | Ohrbom et al. | | |
| 7,060,849 B1 * | 6/2006 | Childress | ............... | C07F 7/1892 556/414 |
| 7,141,618 B2 | 11/2006 | Schneider et al. | | |
| 7,385,069 B2 * | 6/2008 | Rudinger | ............... | B01J 8/0055 556/400 |
| 8,158,818 B2 * | 4/2012 | Stanjek | ................. | C07F 7/1892 560/345 |
| 8,470,951 B2 | 6/2013 | Maliverney | | |
| 8,871,963 B2 * | 10/2014 | Stanjek | ................. | C07F 7/1892 556/420 |
| 2004/0049064 A1 * | 3/2004 | Kammel | ............... | C07F 7/1892 556/414 |
| 2004/0249179 A1 * | 12/2004 | Kornek | ................. | C07F 7/1892 556/414 |
| 2006/0276644 A1 * | 12/2006 | Childress | ............... | C07F 7/1892 544/193 |
| 2015/0274760 A1 * | 10/2015 | Spyrou | ................. | C07F 7/1836 528/26 |

FOREIGN PATENT DOCUMENTS

DE  3544601 C2  11/1992

OTHER PUBLICATIONS

Kammel et al. "New organofunctional Silanes for Adhesives, Sealants and Spray Foams" Organosilicon Chemistry V, 2003, 9 pages.*
Search Report and Written Opinion dated Oct. 1, 2015.

* cited by examiner

*Primary Examiner* — Robert S Loewe
(74) *Attorney, Agent, or Firm* — James C. Abruzzo

(57) ABSTRACT

The invention herein is directed to a process for producing isocyanatoorganosilanes having low color and improved color stability over known isocyanatosilanes involving a neutralizing step in which a carbamatoorganosilane intermediate is neutralized with acid to a pH equal to or greater than 6.0, to the isocyanatosilane produced by said process and to coatings and numerous other industrial applications which are useful in numerous industries containing the isocyanatoorganosilane produced by the process.

19 Claims, No Drawings

PROCESS FOR PRODUCING LOW-COLOR AND COLOR-STABLE ISOCYANATOORGANOSILANES AND PRODUCTS DERIVED THEREFROM

This application claims priority to Provisional U.S. Patent Application No. 62/024,030, which was filed on Jul. 14, 2014, the entire contents of which are incorporated herein by reference in its entirety.

FIELD OF INVENTION

The invention relates to a process for producing isocyanatoorganosilane. Particularly, the invention relates to a process of producing low-color and color-stable isocyanatoorganosilanes which can be used in the non-limiting example of coatings, e.g., clear coatings for automotive applications; and numerous other industrial applications such as in paints, varnishes, powder coatings, printing inks, plastics, ceramic materials, paper, glasses or security devices, formation of elastomer materials, adhesives, and sealants such the production of sealant materials for insulated glass units and other architectural applications.

BACKGROUND OF THE INVENTION

A variety of commercial clear coating compositions are known which employ isocyanatoorganosilanes. These isocyanatoorganosilanes are incorporated into clear coats by reaction with a polyol to form a silylated polymer. During cure, the alkoxysilyl groups of the silylated polymer hydrolyze in the presence of moisture to generate silanols and the silanols condense to form siloxanes and to crosslink the silylated polymer. To be most useful in a clear coating composition, the components thereof should be highly transparent and have low color and high color stability.

Methods for producing isocyanatoorganosilanes from the cracking of silylorganocarbamates are well known. These silylorganocarbamates are typically made by the reaction of aminoorganosilanes and carbonate esters. Unfortunately, however, this reaction of aminoorganosilanes and carbonate esters can also form byproducts. These undesirable byproducts can be carried through to the carbamate cracking process and cause color stability issues of the corresponding isocyanatoorganosilanes, especially upon prolonged storage conditions, which can undesirably increase the color or negatively impact the color stability of the various applications for isocyanatoorganosilanes, such as those applications described herein.

SUMMARY OF THE INVENTION

The present invention provides a process for producing silylorganocarbamates to be used in a thermal cracking process producing isocyanatoorganosilanes that have low-color and improved color-stability over known isocyanatosilanes.

In one embodiment herein there is provided a process for producing low-color and color-stable isocyanatoorganosilane. The process comprises:
(a) reacting aminoorganosilane with organic carbonate ester in the presence of a basic catalyst to form a reaction mixture containing silylorganocarbamate;
(b) neutralizing the reaction mixture of step (a) with an acid to a pH value equal to or greater than 6.0;
(c) stripping the neutralized reaction mixture resulting from step (b) at a temperature of from about 80° C. to about 130° C. so as to provide less than about 5.0 weight percent, more specifically less than about 0.5 weight percent, and even more specifically less than about 0.1 weight percent organic carbonate ester based on the total weight of the stripped reaction mixture;
(d) filtering the stripped reaction mixture resulting from step (c);
(e) optionally adding an acid to adjust the pH of the filtered reaction mixture resulting from step (d) to a value equal to or greater than about 6.0;
(f) thermally cracking the stripped reaction mixture containing silylorganocarbamate resulting from step (d) or step (e) to provide for an isocyanatoorganosilane and thermally cracked reaction byproducts;
(g) separating isocyanatoorganosilane from the thermally cracked reaction byproducts produced in step (f); and
(h) collecting the isocyanatoorganosilane from step (g) to provide for isocyanatoorganosilane having low color and color stability.

The pH value is determined using a pH meter equipped with a combination electrode. The combination electrode comprises a sensing part of electrode which is a bulb made from glass, an internal electrode, specifically a silver chloride electrode or calomel electrode, internal solution, specifically a pH=7 buffered solution of 0.1 mole per liter potassium chloride, a reference electrode containing a 0.1 mole per liter potassium chloride reference internal solution, a junction made from ceramics to the solution to be analyzed and a body of electrode, made from non-conductive glass or plastics. The neutralized reaction mixture of step (b) or step (e) (10 grams) is dissolved in 60 milliliters of a solvent comprised of 62.5 percent by volume of isopropanol and 37.5 percent by volume of deionized water in volume. The pH of the solution is determined by placing the pH electrode into the solution, stirring the solution at room temperature, e.g. 25° C., and reading the value of pH from the meter.

DETAILED DESCRIPTION OF THE INVENTION

In accordance with the invention, it has been discovered that by controlling the pH value of the reaction mixture containing silylorganocarbamate to a value equal to or greater than about 6.0, more specifically from about 6.0 to about 9.0, and even more specifically from about 6.3 to about 7.3, following the reaction of aminoorganosilane and organic carbonate ester; conducting a vacuum stripping at an elevated temperature in the range of 80° C. to 130° C. followed by filtering the product, provides a silylorganocarbamate, which silylorganocarbamate can then be thermally cracked, and the isocyanaotoorganosilane can be separated from the other byproducts of the cracking step, (e.g., through distillation) to produce isocyanatoorganosilanes with low-color and improved color-stability. These isocyanatoorganosilanes are very useful for coating compositions, such as for clear coating compositions for use on automobile parts and in automotive applications, as well as any of the other industrial applications described herein.

In one specific embodiment herein, it will be understood that all ranges herein can comprise all ranges there between, and any combination of endpoints of said ranges and/or subranges thereof.

In one embodiment herein the aminoorganosilane is of the general formula (1):

$(R^2O)_{3-n}R^3_n SiR^1 NH_2$ (1)

wherein
$R^1$ is a divalent hydrocarbon group of from 1 to about 20 carbon atoms, more specifically from 1 to about 12 carbon atoms, even more specifically from 1 to about 8 carbon atoms and most specifically from 1 to about 6 carbon atoms, each $R^2$ and $R^3$ is independently selected from the group consisting of an alkyl group containing from 1 to about 20 carbon atoms, more specifically from 1 to about 12 carbon atoms, even more specifically from 1 to about 8 carbon atoms and most specifically from 1 to about 3 carbon atoms, an alkoxyalkyl group containing from 3 to about 20 carbon atoms, more specifically from 3 to about 12 carbon atoms, even more specifically from 3 to about 8 carbon atoms and most specifically from 3 to about 6 carbon atoms, alkyl groups substituted with at least one halo group containing from 1 to about 10 carbon atoms, a cycloalkyl group containing from 5 to about 10 carbon atoms, an aryl group containing from 6 to about 10 carbon atoms, and an aralkyl group containing from 7 to about 10 carbon atoms; and the subscript n is an integer of from 0 to 2, more specifically 0 or 1, and even more specifically 0.

In one embodiment, the values of $R^1$ is selected from the group consisting of methylene, ethylene, 1,2-propylene, 1,3-propylene, 2-methyl-1,3-propylene, 3-methyl-1,3-propylene, 3,3-dimethyl-1,3-propylene, ethylidene, isopropylidene, 3-methyl-1,4-butylene and 3,3-dimethyl-1,4-butylene, $R^2$ is selected from the group consisting of methyl, ethyl, propyl and isopropyl, $R^3$ is methyl and n is 0 or 1.

Representative and non-limiting examples of aminoorganosilane include, for example, 3-aminopropyltrimethoxysilane, 3-aminopropyldimethylmethoxysilane, 3-aminopropylmethyldimethoxysilane, 3-(aminopropyl)ethyldimethoxysilane, 3-aminopropyltriethoxysilane, 3-aminopropyldimethylethoxysilane, 3-aminopropylphenyldimethoxysilane, 2-aminoethyltriethoxysilane, 4-aminobutyltriethoxysilane, 4-aminobutyltrimethoxysilane, 4-aminobutylmethyldimethoxysilane, 4-(trimethoxysilyl)-2-butanamine, 3-[diethoxy(hexyloxy)silyl]-1-propanamine, 3-[tris(pentyloxy)silyl]-1-propanamine, 3-[tris(2,2,2-trifluoroethoxy)silyl]-1-propanamine, 3-[tris[2-(2-phenoxyethoxy)ethoxy]silyl]-1-propanamine, 3-[tris[(2-ethylhexyl)oxy]silyl]-1-propanamine, 3-[tristhexyloxy)silyl]-1-propanamine, 3-triisopropoxysilylpropylamine, 3-[tris(3-methylbutoxy)silyl]-1-propanamine, 3-[tris(2-ethoxyethoxy)silyl]-1-propanamine, 3-[bis(1,1-dimethylethoxy)methoxysilyl]-1-propanamine, 3-[(1,1-dimethylethoxy)diethoxysilyl]-1-propanamine, 3-[(1,1-dimethylethoxy)dimethoxysilyl]-1-propanamine, 3-(trimethoxysilyl)-1-pentanamine, 4-amino-3,3-dimethylbutyltrimethoxysilane, 4-amino-3,3-dimethylbutyltriethoxysilane, and the like. The aminoorganosilane can be made by any commercially available method.

In one embodiment the organic carbonate ester is of the general Formula (2):

$$R^4OC(=O)OR^4 \qquad (2)$$

wherein each $R^4$ is independently a hydrocarbyl group containing up to about 20 carbon atoms, more specifically from 1 to about 12 carbon atoms, even more specifically from 1 to about 8 carbon atoms and most specifically from 1 to about 6 carbon atoms or halohydrocarbyl group of up to about 20 carbon atoms, more specifically from 1 to about 12 carbon atoms, even more specifically from 1 to about 8 carbon atoms, and most specifically from 1 to about 6 carbon atoms, or both $R^4$ groups together form a divalent alkylene group $R^5$ containing from about 2 to about 12 carbon atoms, specifically from about 2 to about 6 carbon atoms.

Representative and non-limiting examples of organocarbonate esters include, for example, dimethyl carbonate, diethyl carbonate, dipropyl carbonate, diisopropyl carbonate, dibutyl carbonate, dihexyl carbonate, methyl ethyl carbonate, methyl butyl carbonate, diphenyl carbonate, methyl phenyl carbonate, ethylene carbonate, propylene carbonate, and the like and mixtures thereof.

In one embodiment, the organocarbonate ester is dimethyl carbonate or diethyl carbonate.

In one embodiment the basic catalyst herein is an alkoxide (alcoholate) of an alkali metal or alkaline earth metal. Examples of useful alkoxides include sodium methoxide, sodium ethoxide, calcium methoxide, calcium ethoxide, sodium propoxide, sodium tert-butoxide, potassium propoxide, potassium tert-butoxide, lithium methoxide, lithium ethoxide, lithium propoxide, lithium tert-butoxide and the like.

The amount of basic catalyst employed in the present invention step (a) ranges from about 0.01 parts by weight to 2 parts by weight per 100 parts by weight of the combined weight of aminoorganosilane and organic carbonate employed in the reaction. In a specific embodiment, the amount of the basic catalyst ranges from about 0.1 to 0.6 parts by weight per 100 parts by weight of the combined weight of aminoorganosilane and organic carbonate.

The reaction of the aminoorganosilane and organic carbonate is mildly exothermic. The process step (a) can be carried out at ambient, sub-atmospheric or super-atmospheric pressure. The process step (a) can be carried out in either a batch or continuous-feeding process of adding either the aforementioned mixture of aminoorganosilane and basic catalyst to the organocarbonate ester all at once, or through a gradual feeding of the organocarbonate ester that can last from about 5 minutes to up to about 24 hours, more specifically from 1 hour to 10 hours and even more specifically from 1 hour to 4 hours. Optionally, the continuous feeding is accompanied by the recycling of excess organocarbonate ester.

In one embodiment herein the molar ratio of organic carbonate ester to aminoorganosilane in step (a) is from about 1.0/1 to about 1.3/1, more specifically from about 1.05/1 to about 1.2/1 and most specifically from about 1.1/1 to about 1.15/1.

In one embodiment, the reacting step (a) as described herein, can be conducted at a temperature of from about 10° C. to 120° C., more specifically 25° C. to 80° C., and most specifically from about 20° C. to 50° C. The temperature is maintained within these ranges by cooling using circulating cold water, an ice-bath, dry ice ($CO_2$) bath and/or controlling the rate of addition of one or both of the reactants or by other means known to those skilled in the art. If the reaction is conducted at higher temperatures, undesirable by-products, such as other amines and water can form. Generally, the reaction is conducted at ambient pressure under an atmosphere of a dry (i.e., no water) inert gas such as nitrogen or argon. This reaction can optionally be conducted at subatmospheric pressure to control the reaction temperature.

In one embodiment the silylorganocarbamate produced in the reaction of aminoorganosilane and organocarbonate esters is of the general Formula (3):

$$(R^2O)_{3-n}R^3{}_nSiR^1NHC(=O)OR^6 \qquad (3)$$

wherein $R^1$ is a divalent hydrocarbon group of from 1 to about 20 carbon atoms, more specifically from 1 to about 12 carbon atoms, even more specifically from 1 to about 8 carbon atoms and most specifically from 1 to about 6 carbon atoms, each $R^2$ and $R^3$ is independently selected from the group consisting of an alkyl group containing from 1 to about 20 carbon atoms, more specifically from 1 to about 12 carbon atoms, even more specifically from 1 to about 8 carbon atoms and most specifically from 1 to about 3 carbon atoms, an alkoxyalkyl group containing from 3 to about 20 carbon atoms, more specifically from 3 to about 12 carbon atoms, even more specifically from 3 to about 8 carbon atoms and most specifically from 3 to about 6 carbon atoms, an alkyl group substituted with at least one halo group, more specifically a fluoro group, containing from 1 to 10 carbon atoms, a cycloalkyl group containing from 5 to about 10 carbon atoms, an aryl group containing from 6 to about 10 carbon atoms and an aralkyl group containing from 7 to about 10 carbon atoms;

$R^6$ is $R^4$ or $R^5OH$, wherein $R^4$ is a hydrocarbyl group containing up to about 20 carbon atoms, more specifically from 1 to about 12 carbon atoms, even more specifically from 1 to about 8 carbon atoms and most specifically from 1 to about 6 carbon atoms or a halohydrocarbyl group containing up to about 20 carbon atoms, more specifically from 1 to about 12 carbon atoms, even more specifically from 1 to about 8 carbon atoms, and most specifically from 1 to about 6 carbon atoms, and $R^5$ is an alkylene group containing from about 2 to about 12 carbon atoms, specifically from about 2 to about 6 carbon atoms;

and the subscript n is an integer of from 0 to 2, more specifically 0 or 1, and even more specifically 0.

In one non-limiting embodiment, the $R^1$ is selected from the group consisting of methylene, ethylene, 1,2-propylene, 1,3-propylene, 2-methyl-1,3-propylene, 3-methyl-1,3-propylene, 3,3-dimethyl-1,3-propylene, ethylidene, isopropylidene, 3-methyl-1,4-butylene and 3,3-dimethyl-1,4-butylene; $R^2$ is selected from the group consisting of methyl, ethyl, propyl and isopropyl; $R^3$ is methyl; $R^6$ is selected from the group consisting of methyl, ethyl propyl and isopropyl and n is 0 or 1.

Representative and non-limiting examples of $R^1$ include methylene, ethylene, 1,2-propylene, 1,3-propylene, 2-methyl-1,3-propylene, 3-methyl-1,3-propylene, 3,3-dimethyl-1,3-propylene, ethylidene, isopropylidene, 3-methyl-1,4-butylene, 3,3-dimethyl-1,4-butylene, and the like;

Representative and non-limiting examples of $R^2$ and $R^3$ include methyl, ethyl, propyl, isopropyl, butyl, tert-butyl, isobutyl, pentyl and dodecyl.

Representative and non-limiting examples of $R^6$ include methyl, ethyl, propyl and isopropyl.

Specific N-silylorganocarbamates that can be prepared in accordance with the invention herein include N-(3-trimethoxysilylpropyl)methylcarbamate, [3-(triethoxysilyl) propyl]-carbamic acid nonadecyl ester, [3-(triethoxysilyl) propyl]-carbamic acid 2-[2-(2-methoxyethoxy)ethoxy]ethyl ester, carbonic acid 1,1-dimethylethyl 3-[[[[3-(triethoxysilyl)propyl]amino]carbonyl]oxy]phenyl ester, [3-(triethoxysilyepropyl]-carbamic acid 3-phenyl-2-propenyl ester, [3-(triethoxysilyl)propyl]-carbamic acid 3,3-diphenyl-3H-naphtho[2,1-b]pyran-9-yl ester, [3-(ethoxydimethoxysilyl) propyl]-carbamic acid methyl ester, [3-(diethoxymethoxysilyl) propyl]-carbamic acid methyl ester, [3-(triethoxysilyl)propyl]-carbamic acid 3,3,4,4,5,5,6,6,7,7,8,8,8-tridecalluorooctyl ester, [3-(triethoxysilyl)propyl]-carbamic acid 1,3,5-benzenetriyltris(methylene) ester, [3-(triethoxysilyl)propyl]-carbamic acid 1,3,5-benzenetriyltris(methylene) ester, [3-(triethoxysilyl)propyl]-carbamic acid phenylmethyl ester, [3-(trimethoxysilyl)propyl]-carbamic acid ethyl ester, [3-(trimethoxysilyl)propyl]-carbamic acid 1,1-dimethylethyl ester, [3-(triethoxysilyl) propyl]-carbamic acid 1,1-dimethylethyl ester, [3-(trimethoxysilyl)propyl]-carbamic acid methyl ester and [3-(triethoxysilyl)propyl]-carbamic acid ethyl ester.

Following reaction step (a), the reaction mixture containing silylorganocarbamate can be neutralized with an acid to a pH equal to or greater than 6.0, more specifically from about 6.0 to about 9.0, and even more specifically from about 6.3 to about 7.3, i.e., step (b). Suitable acids that may be employed in neutralization step (b) are any Lewis acids/Bronsted acids and more specifically includes inorganic acids such as anhydrous phosphoric acids or sulfuric acid, or zeolites and most preferably organic acids. Representative and non-limiting examples include glacial acetic acid, propionic acid, butyric acid, hexanoic acid, oleic acid, maleic acid, fumaric acid, succinic acid, benzene sulfonic acid, ion exchange resins, and the like, and mixtures thereof. The absence of water in the inventive process is desirous to avoid unwanted reactions and byproducts. The process step (b) can be carried out at ambient, sub-atmospheric or super-atmospheric pressure. The process step (b) can be carried out in either a batch or continuous-feeding process. In one embodiment, step (c) can be carried out so as to provide less than about 5.0 weight percent organic carbonate ester based on the total weight of the stripped reaction mixture. In an embodiment, the stripping step (c) can be carried out in one or more steps.

Following step (b) or during step (b), the neutralized reaction mixture can be stripped in a vacuum at a temperature of from about 80° C. to about 130° C. (i.e., step (c)) more specifically from about 100° C. to about 125° C. and most specifically from about 110° C. to about 125° C. In one embodiment, the vacuum can be applied up to about 90 mmHg, more specifically from about 0.1 mmHg to about 75 mmHg and even more specifically from about 10 mmHg to about 50 mm Hg. The stripping step (c) can be conducted for a time sufficient to remove the alcohol byproduct produced in the reaction of aminoorganosilane and organocarbonate ester, as well as any unreacted organocarbonate ester, which unreacted organocarbonate ester can be recycled to the process. The process step (c) can be carried out in either a batch or continuous-feeding process. In one embodiment, step (c) can be carried out so as to provide less than about 5.0 weight percent organic carbonate ester based on the total weight of the stripped reaction mixture. In an embodiment, the stripping step (c) can be carried out in one or more steps.

Following the stripping step (c), the stripped reaction mixture resulting from step (c) can be filtered by any known means, e.g., vacuum or pressure filtration using well known filtering aids such as Celite and filtering paper. This filtration can be conducted under a blanket of pressurized dry inert gas such as nitrogen or argon. The filtration can be conducted at the temperature ranges described herein or in one embodiment at ambient temperature. In two-step stripping, higher vacuum and $N_2$ spurge applied in the second step helps to removed impurities which are not able to be removed by the first stripping step. In one embodiment, the filtering step (e) is such that the silylorganocarbamate is separated from the reaction mixture.

In one non-limiting embodiment herein, the filtered reaction mixture resulting from step (d) can optionally have an acid added thereto to adjust the pH of the filtered reaction resulting from step (d) to a value equal to or greater than about 6.0, more specifically from about 6.0 to about 9.0, and even more specifically from about 6.3 to about 7.3, i.e., step (e)

After completion of the filtering step (d), or optional step (e), the silylorganocarbamate is thermally cracked to produce an isocyanatoorganosilane, i.e., step (f) The cracking step of the process of the invention can be carried out by heating the stripped silylorganocarbamate-containing reaction mixture from step (d), or optional step (e), under suitable cracking conditions, e.g., elevated temperature and subatmospheric pressure, for a sufficient period of time for conversion of silylorganocarbamate to isocyanatoorganosilane to take place. Gas phase or liquid phase cracking conditions can be utilized.

In one embodiment, the cracking reaction zone is operated under gas phase conditions and cracking reaction medium is purged from the bottom of an apparatus associated with the cracking reaction zone. In another embodiment, the cracking reaction zone is operated under liquid phase conditions and cracking reaction medium is purged from the cracking reaction zone.

In one embodiment herein, the apparatus used in the cracking step (f) can be any apparatus having the capacity for maintaining an inert atmosphere or a reduced pressure, for maintaining a liquid level and having the capacity to heat the liquid to the desired temperature range, the ability to feed the silylorganocarbamate into the heated liquid or heated gas, for removing any alcohol byproduct, a column for rectification of the product, if needed, and condensing the desired isocyanatoorganosilane. In another embodiment a distillation column or rectification column is attached to a reactor which separates the volatile isocyantoorganosilane from the reaction zone (cracking zone) and which optionally returns unreacted silylorganocarbamate, if any, to the reaction zone (cracking zone). Moreover any alcohol produced, a thermal cracking byproduct of the cracking reaction, is separated from the isocyanatoorganosilane product and allowed to pass through the condenser.

The reaction can generally be described by the following equation:

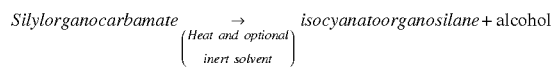

While an inert organic solvent or mixture of solvents can be employed, there is no requirement to do so. Some examples of such optional solvents are linear or branched alkanes, esters, ethers, cycloaliphatic and aromatic hydrocarbons, fluorocarbons, fluorocarbon ethers, and silicone fluids.

The cracking conditions are dependent upon the particular silylorganocarbamate reactant and, if employed, the particular optional cracking catalyst, used in the process. Residence times range from about 1 minute up to about 24 hours, advantageously from about 15 minutes up to about 5 hours. In one embodiment, the silylorganocarbamate is cracked by heating it to reflux under reduced pressure to provide for the initial separation of the aliphatic monohydric alcohol. The alcohol is captured in a cold trap, such as a dry ice trap, ice trap or trap cooled with refrigerated liquids. With proper adjustment of the reflux ratio, there can be achieved continuous cracking of the silylorganocarbamate, and continuous separation of the silylorganoisocyanate as an overhead product. The cracking temperature of the silylorganocarbamate and the proper reflux ratio can be best determined by initially bringing the silylorganocarbamate to reflux in a suitable fractionating column under reduced pressure, while providing for the continuous separation of the aliphatic monohydric alcohol.

The cracking step (f) is in one embodiment conducted at a temperature of from about 160° C. to about 230° C., more specifically 190° C. to about 225° C. In another embodiment, the cracking step (f) can be conducted under a reduced pressure which ranges from about 5 mmHg to about 200 mmHg, more specifically from about 10 to about 100 mmHg, and even more specifically from about 15 to about 75 mmHg.

In one non-limiting embodiment, the silylorganocarbamate in step (f) is optionally contacted with a cracking catalyst. The optional cracking catalyst can be added to facilitate thermal dissociation of the silylorganocarbamate to alcohol and the silylorganoisocyanate. However, strongly basic cracking catalysts such as sodium methoxide are not preferred due to a tendency to form colored and highly viscous products. The cracking catalysts optionally used herein are generally well known and readily commercial available. Suitable for use as the optional cracking catalyst in the process herein are compounds of the general Formula (4):

wherein $M^1$ is selected from the group consisting of aluminum, titanium, magnesium and zirconium; and, each $R^7$ is the same or different and is independently a monovalent hydrocarbon group having from 1 to 8 carbon atoms, more specifically from 1 to about 4 carbon atoms, where the subscript x is an integer of from 2 to 4.

Illustrative of such optional cracking catalysts which can be used herein are aluminum alkoxides, titanium alkoxides, magnesium alkoxides, and zirconium alkoxides. Suitable aluminum alkoxides for use can include aluminum trimethoxide, aluminum triethoxide, aluminum triisopropoxide, aluminum tri-sec-butoxide, aluminum tri-tert-butoxide and the like. Suitable titanium alkoxides for use can include titanium (IV) methoxide, titanium (IV) ethoxide, titanium (IV) isopropoxide, titanium (IV) butoxide, titanium (IV) 2-ethylhexoxdde and the like. Suitable zirconium alkoxides can include zirconium (IV) ethoxide, zirconium (IV) propoxide, zirconium (IV) butoxide, zirconium (IV) isopropoxide, zirconium (IV) tert-butoxide, and the like. Suitable magnesium alkoxides can include magnesium methoxide, magnesium ethoxide, magnesium butoxide, magnesium propoxide, and magnesium phenoxide. More specific optional cracking catalysts for use in the present invention are the aluminum alkoxides. A most specific optional cracking catalyst is aluminum triethoxide.

Alternatively, a tin-containing compound can be used as an optional cracking catalyst in the present invention. Illustrative of such optional tin-containing compounds can include organotin carboxylates such as, for example, dibutyltin dilaurate, dibutyltin diacetate, dibutyltin bis(2-ethylhexanoate). Other organotin compounds such as, for example, dibutyltin oxide, dibutyltin dimethoxide, dibutyltin dibromide, dibutyltin dichloride, di-tert-butyltin dichloride, dimethyltin dibromide, dimethyltin dichloride, diphenyltin dichloride, and stannous octoate. More specific among these tin-containing compounds are dibutyltin dilaurate, dibutyltin oxide, dibutyltin diacetate, and stannous octoate.

The amount of the optional cracking catalyst employed in the present invention can be readily determined by one skilled in the art. In one embodiment, the amount of optional cracking catalyst ranges from about 0.01 percent by weight to 5 percent by weight, more specifically from about 0.5 percent by weight to 0.2 percent by weight based upon the total amount of the silylorganocarbamate.

Following the cracking of step (f), the isocyanatoorganosilane is separated from the thermally cracked silylorganocarbamate byproducts (i.e., step (g)) by any means available, such as in one non-limiting embodiment by distillation, which is then is followed by collecting the isocyanatoorganosilane having low color and color stability, i.e. step (h), for example by collecting the distillation-separated isocyanatoorganosilane of step (g) using known means.

In one non-limiting embodiment the isocyanatoorganosilane produced by the process described herein, e.g., steps (a)-(h), has a purity of greater than 90 percent by weight, more specifically greater than 92 percent by weight, and most specifically greater than 94 by weight, based upon the total weight of the distillate collected in step (h). The impurities present following the separation of isocyanatoorganosilane from the cracking reaction products, can be unreacted organic carbonate ester and/or unreacted aminoorganosilane as well as unreacted carbamate, cyclic carbamate, amines, trimer of isocyanatosilane.

The isocyanatoorganosilane made by any of the process(es) described herein has low color. In one embodiment, the low color is a value of color, as determined in accordance with ASTM D1209-05, Standard Test Method for Color of Clear Liquids (Platinum-Cobalt Scale), of less than about 100 Pt—Co, more specifically, less than about 20 Pt—Co, and even more specifically, less than 10 Pt—Co.

In one non-limiting embodiment, the isocyanatoorganosilane produced by the process steps (a)-(h) herein, has a color stability which is defined as the change in the color, where the change in color is the color of the isocyanatoorganosilane after the isocyanatoorganosilane is aged at 100° C. for 24 hours minus the color of the isocyanatoorganosilane as produced in process steps (a)-(h). The color is determined in accordance with ASTM D1209-05, Standard Test Method for Color of Clear Liquids (Platinum-Cobalt Scale). The color stability of the isocyanatoorganosilane is equal to or less than 40 Pt—Co, more specifically, less than 25 Pt—Co, and most specifically less than 20 Pt—Co.

In one embodiment, the isocyanatoorganosilane of step (h) can be treated with a resin. Representative and non-limiting examples of such resins include ion-exchange resins, such as polymeric, macroporous solid acids, such as the non-limiting example of Purolite resins, e.g., Purolite CT 275, or absorbers such as activated carbon. The optional treating of the isocyanatoorganosilane with a resin can comprise optionally filtering the separated isocyanatoorganosilane through the resin, optionally using vacuum or pressure.

In another embodiment, isocyanatoorganosilane having low color and color stability is made by the process of the present invention. The isocyanatoorganosilane made by any of the process(es) described herein has color stability due to the absence of impurities and undesirable byproducts which are eliminated by the process steps described herein.

In one non-limiting embodiment herein there is also provided a coating composition comprising the isocyanatoorganosilane made by the process described herein. The coating composition can be a coating composition suitable for automotive or industrial coating, such as the non-limiting example of an automotive clear coat composition. Coating compositions and automotive coating compositions are well known in the art and will not be discussed in detail herein. A typical vehicle has several coating layers. The substrate is typically first coated with an inorganic rust-proofing zinc or iron phosphate layer over which is applied an electrocoated primer or repair primer. Optionally, a primer surfacer can be employed for better appearance and improved adhesion. A pigmented basecoat or colorcoat is next applied over the primer. A typical basecoat or colorcoat may contain metallic flakes to provide a metallic finish. To protect and preserve the aesthetic qualities of the color finish, a clear (un-pigmented) topcoat (i.e., a clear-coat) is often applied over the pigmented basecoat to protect the basecoat even on prolonged weathering. Clear coats are predominantly based on a technology where the binders are hydroxy functional acrylics crosslinked with alkoxylated melamine formaldehyde adducts. The coatings are typically baked at about 130° C. after application wet-on-wet on a basecoat and can also contain isocyanatosilane, and optionally, other silane-functional polymers.

The coating compositions of the invention can be applied to a variety of substrates, for example automotive substrates such as fenders, hoods, doors and bumpers, and industrial substrates such as household appliances, including washer and dryer panels and lids, refrigerator doors and side panels, lighting fixtures and metal office furniture; as well as floor coverings such as ceramic tiles and wood flooring. The automotive and industrial substrates can be metallic, for example, aluminum and steel substrates, and non-metallic, for example, thermoplastic or thermoset (i.e. "polymeric") substrates including, for example, transparent plastic substrates, polycarbonate, and polymethyl methacrylate and elastomeric substrates such as thermoplastic polyolefin. Wood substrates are also suitable for coating with the present compositions. As stated above, the coating compositions of the invention are particularly useful as top coats and/or clear coats in color-clear composite coatings. The compositions of the invention in the pigmented form can be applied directly to a substrate to form a color coat. Alternately, the coating composition of the invention can be un-pigmented, in the form of a clear coat for application over a color coat (either a primer coat or a colored topcoat). When used as a color topcoat, coating thicknesses of about 0.5 to 5.0 mils are usual, and when used as a clear coat, coating thicknesses of about 1.0 to 4.0 mils are generally used.

In another embodiment, the isocyanatoorganosilanes described herein can be used in printing which also permits, by virtue of the machine readability of markings, the use for security applications, for example for tickets, forgery-proof labels for high-value goods or other documents. In addition, the isocyanatoorganosilanes made by the process(es) described herein can also be used in various other applications such as a traffic light element, a frame, a profile, a molding of complex geometry, a guideboard element, radiator element or fencing element, a part made from or with at least one pipe and/or one profile, a window frame, door frame or cycle frame, or a small part such as, for example, a bolt, nut, flange, spring or a spectacle frame. The substrates coated in accordance with the invention may be used in particular in the vehicle, air travel or space travel industry, in architecture or in appliance construction, especially for household appliances. Further, the isocyanatoorganosilanes can be used in the manufacture of elastomeric materials, which elastomeric materials are utilized in the manufacture of various hoses, seals, mounting, damping and insulating devices such as those in architectural and automobile applications, such as those found in the engine compartments of automobiles and other vehicles. In addition, devices for mounting the engines within these vehicles typically comprise one or more metal parts adhesively bonded to one or more vulcanized elastomeric parts. Further, still isocyanatoorganosilanes can be used in the formation of silylated polyurethane resin which can be used in adhesives, coatings and sealants, such for example, the non-limiting example of a sealant material for insulated glass units and the like.

Accordingly, the present invention is further directed to a substrate coated with one or more of the present coating compositions described herein which contain the isocyanatoorganosilane made by the process described herein.

In yet another embodiment, the present invention is directed to a method for improving the mar and/or scratch resistance of a coated substrate comprising applying the present compositions to at least a portion of the substrate. Application can be by any means known in the art to the thicknesses described above. The coatings formed according to the present invention, when cured, can have outstanding appearance properties and scratch and mar resistance properties.

The disclosure herein will now be described in conjunction with the following examples which are to be regarded as being illustrative of certain embodiments of the disclosure herein but should not be viewed to restrict the disclosure. All percents herein are weight percents based on the total weight of composition unless indicated otherwise.

EXAMPLES

The following examples are illustrative of the process of the invention. The general procedure for making carbamatosilanes of Examples 1 through 3 and Comparative Examples A and B is described as the following. The thermal cracking of carbamatosilanes procedure is described in Example 4.

Example 1

Preparation of 3-Isocyanatopropyltrimethoxysilane Using N-Trimethoxysilylpropylmethylcarbamate Having a pH of 6.50

In a STR reactor, dimethylcarbonate (2405 kilograms) and the basic catalyst (0.26 percent by weight basic catalyst, 30% sodium methylate solution in methanol, based on the total weight of dimethylcarbonate and gamma-aminopropyltrimethoxysilane) was charged into the stir tank reactor and heated to 40° C. with agitation. Over a period of time, gamma-aminopropyltrimethoxysilane (4433 kilograms) was added continuously into the reactor.

After addition, the mixture was heated to 45±5° C. and held for 4 hours. The solution was then cooled down to 40° C., and neutralized with glacial acetic acid to control pH value of the mixture in the range of 6.0-7.0. The mixture was then stripped at less than 75 mmHg and 120-125° C. to remove volatile organic components. The mixture was then filtered. Glacial acetic acid was added to adjust the pH value to the values reported in Table 1. The isolated N-trimethoxysilylpropylmethylcarbamate was analyzed by gas chromatography.

The resulting N-trimethoxysilylpropylmethylcarbamate was then thermally cracked in a reactor equipped with a mechanical agitator and a packed a distillation column, followed by a water condenser to obtain gamma-isocyanatopropyltrimethoxysilane product. The reaction was carried at a temperature in the range of 210° C. to 225° C., and a vacuum of 60 to 70 mmHg. The reflux ratio was adjusted to maintain the purity. The sample was analyzed by GC to determine the purity. Color stability testing was performed using 50 grams of the reaction product heated at 100° C. for 24 hours followed by solution color measurement (Pt—Co scale) in accordance with ASTM D1209-05, Standard Test Method for Color of Clear Liquids (Platinum-Cobalt Scale).

Example 2

Preparation of 3-isocyanatopropyltrimethoxysilane using N-trimethoxysilylpropylmethylcarbamate Having a pH of 6.21

The isocyanatopropyltrimethoxysilane was prepared in a similar manner to Example 1, except that the pH of N-trimethoxysilylpropylmethylcarbamate was adjusted to 6.21.

Example 3

Preparation of 3-isocyanatopropyltrimethoxysilane using N-trimethoxysilylpropylmethylcarbamate Having a pH of 6.40

The isocyanatopropyltrimethoxysilane was prepared in a similar manner to Example 1, except that the pH of N-trimethoxysilylpropylmethylcarbamate was adjusted to 6.40.

Comparative Example A

Preparation of 3-isocyanatopropyltrimethoxysilane using N-trimethoxysilylpropylmethylcarbamate Having a pH of 5.30

The isocyanatopropyltrimethoxysilane was prepared in a similar manner to Example 1, except that the pH of N-trimethoxysilylpropylmethylcarbamate was adjusted to 5.30.

Comparative Example B

Preparation of 3-isocyanatopropyltrimethoxysilane using N-trimethoxysilylpropylmethylcarbamate Having a pH of 5.0

The isocyanatopropyltrimethoxysilane was prepared in a similar manner to Example 1, except that the pH of N-trimethoxysilylpropylmethylcarbamate was adjusted to 5.00.

The isocyanatosilane product aged color results for Examples 1 through 3 and Comparative examples A and B were shown in Table 1. It is clear that isocyanatosilane produced by the improved process in the present invention had low color and the improved color stability.

TABLE 1

Data on the color and color stability of 3-isocyanatopropyltrimethoxysilane made by the process of the present invention and comparative processes.

| | Carbamatosilane pH | Isocyanatosilane sample | | | | |
|---|---|---|---|---|---|---|
| | | Sample # | Purity, % | Color Pt—Co | Heat Aged Color (100° C., 24 h), Pt—Co | Color stability |
| Example 1 | 6.50 | 1 | 94.08 | 0.0 | 10 | 10 |
| | | 2 | 94.81 | 3.4 | 9 | 5.6 |

TABLE 1-continued

Data on the color and color stability of 3-isocyanatopropyltrimethoxysilane made by the process of the present invention and comparative processes.

| | Carbamatosilane pH | Isocyanatosilane sample | | | | |
|---|---|---|---|---|---|---|
| | | Sample # | Purity, % | Color Pt—Co | Heat Aged Color (100° C., 24 h), Pt—Co | Color stability |
| Example 2 | 6.21 | 1 | 94.68 | 7.1 | 15 | 7.9 |
| | | 2 | 94.61 | 4.0 | 11 | 7 |
| Example 3 | 6.40 | 1 | 94.40 | 9.8 | 19 | 9.2 |
| | | 2 | 93.64 | 3.5 | 13 | 9.5 |
| Comparative Example A | 5.30 | 1 | 95.34 | 0.0 | 69 | 69 |
| | | 2 | 94.46 | 10.0 | 55 | 45 |
| Comparative Example B | 5.00 | 1 | 94.30 | 2.6 | 45 | 42.4 |
| | | 2 | 94.20 | 6.7 | 105 | 98.3 |

The data in Table 1 indicate that the pH of the N-trimethoxysilylpropylmethyl-carbamate was important in producing 3-isocyanatopropyltrimethoxysilane that was of low color, less than 10 Pt—Co, and had color stability. The color stability was determined by subtracting the color after aging 3-isocyanatopropyltrimethoxysilane at 100° C. for 24 hours from the color of said silane as made. The color stabilities of Examples 1-3 were between 5.6 and 10 Pt—Co. The Comparative Examples A and B had color stability ranging from 42.2 to 98.3.

While the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention but that the invention will include all embodiments falling within the scope of the appended claims.

The invention claimed is:

1. A process for producing isocyanatoorganosilane having low color and color stability comprising:
   (a) reacting aminoorganosilane with organic carbonate ester in the presence of basic catalyst to form a reaction mixture containing silylorganocarbamate;
   (b) neutralizing the reaction mixture of step (a) with an organic carboxylic acid to a pH value equal to or greater than 6.0;
   (c) stripping the neutralized reaction mixture resulting from step (b) at a temperature of from about 80° C. to about 130° C. so as to provide less than about 5.0 weight percent organic carbonate ester based on the total weight of the stripped reaction mixture;
   (d) filtering the stripped reaction mixture resulting from step (c);
   (e) optionally adding an organic carboxylic acid to adjust the pH of the filtered reaction mixture resulting from step (d) to a value equal to or greater than about 6.0;
   (f) thermally cracking the stripped reaction mixture containing silylorganocarbamate resulting from step (d) or step (e) to provide for an isocyanatoorganosilane and thermally cracked reaction byproducts;
   (g) separating isocyanatoorganosilane from the thermally cracked reaction byproducts produced in step (f); and
   (h) collecting the isocyanatoorganosilane from step (g) to provide for isocyanatoorganosilane having low color and color stability.

2. The process of claim 1 wherein the organic carbonate ester is less than about 0.1 percent by weight based on the total weight of the stripped reaction mixture.

3. The process of claim 1 wherein the aminoorganosilane is of the general Formula (1):

$$(R^2O)_{3-n}R^3{}_nSiR^1NH_2 \qquad (1)$$

wherein
  $R^1$ is a divalent hydrocarbon group of from 1 to about 20 carbon atoms;
  each $R^2$ and $R^3$ is independently selected from the group consisting of an alkyl group containing from 1 to about 20 carbon atoms, an alkoxyalkyl group containing from 3 to about 20 carbon atoms, alkyl groups substituted with at least one halo group containing from 1 to about 10 carbon atoms, a cycloalkyl group containing from 5 to about 10 carbon atoms, an aryl group containing from 6 to about 10 carbon atoms and an aralkyl group containing from 7 to about 10 carbon atoms; and
  the subscript n is an integer of from 0 to 2.

4. The process of claim 1 wherein the organic carbonate ester is of the general $$R^4OC(=O)OR^4 \qquad (2)$$

wherein
  each $R^4$ is independently a hydrocarbyl group containing up to about 20 carbon atoms, or a halohydrocarbyl group containing up to about 20 carbon atoms, or both $R^4$ groups together form a divalent alkylene group $R^5$ containing from about 2 to about 12 carbon atoms.

5. The process of claim 1 wherein the basic catalyst is an alkoxide of an alkali metal or alkaline earth metal.

6. The process of claim 1 wherein the silylorganocarbamate is of the general Formula (3):

$$(R^2O)_{3-n}R^3{}_nSiR^1NHC(=O)OR^6 \qquad (3)$$

wherein
  $R^1$ is a divalent hydrocarbon group of from 1 to about 20 carbon atoms;
  each $R^2$ and $R^3$ is independently selected from the group consisting of an alkyl group containing from 1 to about 20 carbon atoms, an alkoxyalkyl group containing from 3 to about 20 carbon atoms, an alkyl group substituted with at least one halo group containing from 1 to about 10 carbon atoms, a cycloalkyl group containing from 5 to about 10 carbon atoms, an aryl group containing from 6 to about 10 carbon atoms, and an aralkyl group containing from 7 to about 10 carbon atoms;

$R^6$ is $R^4$ or $R^5OH$, wherein $R^4$ is a hydrocarbyl group containing up to about 20 carbon atoms, or a halohydrocarbyl group containing up to about 20 carbon atoms, and $R^5$ is an alkylene group containing from about 2 to about 12 carbon atoms;

and the subscript n is an integer of from 0 to 2.

7. The process of claim 1 wherein the molar ratio of organic carbonate ester to aminoorganosilane in step (a) is from about 1.0/1 to about 1.3/1.

8. The process of claim 1 where in step (b) the organic carboxylic acid is selected from the group consisting of glacial acetic acid, propionic acid, butyric acid, hexanoic acid, oleic acid, maleic acid, fumaric acid, succinic acid and mixtures thereof.

9. The process of claim 1 wherein the stripping step (c) is conducted at a temperature of from 80° C. to about 130° C.

10. The process of claim 1 wherein the stripping step (c) is conducted at a vacuum of up to about 90 mmHg.

11. The process of claim 10 wherein the stripping step (c) is conducted in a vacuum of from about 10 mmHg to about 50 mm Hg.

12. The process of claim 1 wherein the stripping step (c) is conducted for a time sufficient to remove alcohol byproduct and unreacted organocarbonate ester.

13. The process of claim 1 wherein the cracking step (f) is conducted at a temperature of from about 160° C. to about 230° C.

14. The process of claim 1 wherein the color stability of the isocyanatoorganosilane collected in step (h) is such that after being exposed to a heat of 100° C. for 24 hours, is equal to or less than 40 Pt—Co, as measured in accordance with ASTM D1209-05.

15. The process of claim 1 further comprising treating the isocyanatoorganosilane collected in step (h) with an ion exchange resin.

16. The process of claim 1 further comprising (i) utilizing the isocyanatosilane (h) in a coating composition.

17. The process of claim 16 wherein the coating composition of is an automotive or industrial coating.

18. The process of claim 17 wherein the automotive coating is an automotive clear coat.

19. The process of claim 1 wherein the neutralizing step (b) is conducted with an organic carboxylic acid to neutralize the silylorganocarbamate reaction product mixture to a pH of from 6.3 to 7.3.

* * * * *